(12) United States Patent
Irving et al.

(10) Patent No.: US 6,864,053 B1
(45) Date of Patent: Mar. 8, 2005

(54) QUANTITATIVE ASSAY OF HOST CELL DNA IN A SAMPLE

(75) Inventors: John M. Irving, San Mateo, CA (US); Kenneth Ho, San Mateo, CA (US); Michael Mok, Palo Alto, CA (US); Flavia Borellini, Foster City, CA (US)

(73) Assignee: Cell Genesys, Foster City, CA (US)

(*) Notice: Subject to any disclaimer, the term of this patent is extended or adjusted under 35 U.S.C. 154(b) by 0 days.

(21) Appl. No.: 09/564,857

(22) Filed: May 4, 2000

(51) Int. Cl.⁷ .................................. C12Q 1/68
(52) U.S. Cl. .................... 435/6; 435/4; 435/5; 435/325
(58) Field of Search .......................... 435/4, 5, 6, 325

(56) References Cited

PUBLICATIONS

Wilkinson 1990 J of Virology vol. 64 (5), pp. 2157–2167.*
Fraser 1988 Genomics 2, pp. 280–287.*
Wilkinson et al., *J Virol* (1990) 64:2157.
Mager et al., *Proc Natl Acad Sci* (1984) 81:7510–7514.
Feuchter et al., *Genomics* (1992) 13:1237–1246.
Fraser et al., *Genomics* (1988) 2:280–287.

* cited by examiner

*Primary Examiner*—James Housel
*Assistant Examiner*—Myron G. Hill
(74) *Attorney, Agent, or Firm*—Steven B. Kelber; DLA Piper Rudnick Gary Cary US LLP

(57) ABSTRACT

Detection of members of a conserved, dispersed gene family is used to ascertain levels of host cell genomic DNA in a sample.

16 Claims, No Drawings

QUANTITATIVE ASSAY OF HOST CELL DNA IN A SAMPLE

FIELD OF THE INVENTION

The invention relates to methods and means for quantifying the amount of host cell nucleic acids, such as mammalian deoxyribonucleic acid (DNA) and particularly human DNA in a sample by detecting the presence of and quantifying the amount of gene family nucleic acid, such as the presence of and amount of human endogenous retrovirus-like (HERV) nucleic acids, in the sample.

BACKGROUND OF THE INVENTION

Cell, tissue and organ culture can be used to produce biologicals, such as, proteins, nucleic acids and viruses. For example, the host cells of the culture naturally may express the product of interest, can be manipulated to express a product of interest, and perhaps at higher than normal levels, or can be transformed to carry and to express a foreign nucleic acid containing the genetic information encoding the product of interest The foreign nucleic acid or translation product thereof can be amplified in the host cells. The foreign nucleic acid can express not only a polypeptide but also a functional ribonucleic acid (RNA), such as an antisense molecule or a ribozyme, viral vectors, regulatory factors and so on.

Cell lines are another source of biological products and can serve as a means for amplifying introduced nucleic acids and obtaining expression products therefrom. The cells can be of random origin or can be obtained from a specific source in view of intended use and/or properties of the desired product.

Using cells and tissues to manufacture or to isolate a desired product may require implementing varying types of purification methods alone or in combination to obtain the product of interest. The range of purification methods implemented depends on, for example, the actual amount of desired product, the desired level of purity, the structural or functional similarity of the desired product to endogenous molecules of the host cell and so on. Thus, purification can entail mere lysis of the host cell or can include subsequent steps including immunoaffinity chromatography, size exclusion chromatography, electrophoretic separation, selective degradation by, for example, an enzyme, and gradient centrifugation.

Following the purification steps, it may be desirable to determine the amount of product present as well as the level of purity thereof. The level of purification can be determined in any of a variety of ways, for example, by determining the amount of specific protein as compared to total protein present in a sample. Alternatively, the amount of a specific contaminant of interest can be determined.

SUMMARY OF THE INVENTION

An object of the instant invention is to provide a method and means for detecting and quantifying the presence of and amount of host cell nucleic acid in a sample by detecting the presence of and amount of gene family nucleic acids, wherein the members of the gene family are dispersed in the host cell genome and can be detected, for example, with a low number of probes or primers. A suitable gene family for use with human cells is the human endogenous retrovirus-like (HERV) gene family.

DETAILED DESCRIPTION OF THE INVENTION

A host cell, tissue or organ used in the practice of the instant invention can be any cell, tissue or organ that contains or produces a product of interest. The host cell can be naturally occurring or can be one that is manipulated to contain or to produce a product of interest. The host cell may be present in a single cell suspension or held in a mass. The host cell, tissue or organ can be maintained in vitro practicing known methods and using known materials.

Also included in the definition of the phrase, "host cell", are cell heterokaryons, chimeras and so on that are combinations of two or more cells where presence of one of the parent cells used to construct the chimera is detectable by the practice of the instant invention. Thus, the chimera may contain human genomic DNA if one of the cells used to make the chimera is a human cell and a human gene family of interest is used as described herein.

Thus, the host cell generally is a eukaryotic cell and is not necessarily restricted so long as the cell carries sequences of a gene family of interest. Generally, the eukaryotic cell contains multiple chromosomes. Suitable host cells are insect cell and plant cells that are used to produce gene products of interest including mammalian gene products and human gene products. Thus, a human protein is synthesized in insect cells or in plant cells, such as tobacco cells. Host cells can be of invertebrate or vertebrate origin. Host cells can be fish cells, amphibian cells, reptile cells, avian cells or mammalian cells. Host cells can be of particular mammalian species, such as mouse or human. The type of host cell is a design choice of the artisan.

Biological products of interest can be isolated and purified from suitable natural sources. For example, human circulatory system products of interest can be obtained from human blood, plasma and serum. Proteins, such as albumin, immunoglobulins and the like, can be obtained from natural sources.

Therefore, for example, antibodies can be purified from human blood tissue. Monoclonal antibodies, and particularly human monoclonal antibodies, can be made in mouse or human cells. Antibodies can be obtained from transformed mouse or human cells that contain nucleic acids encoding particular antibody genes.

Also included in the definition of "host cell" are cells, of any origin, that are configured to contain some particular genomic DNA not endogenous to the host cell, such as a cell that is microinjected with one or more human chromosomes or artificial chromosomes, such as yeast artificial chromosomes (YAC's) containing human DNA inserts.

Host cells that are manipulated to contain or to produce a product of interest are treated to carry a nucleic acid foreign thereto by standard methods. "Foreign" is meant to include any nucleic acid that is introduced into a cell. The foreign nucleic acid can be introduced by infection, precipitation, transfection, transduction, microinjection, electroporation, essentially by any known method.

The foreign nucleic acid encodes a recombinant product of interest, such as a recombinant protein, recombinant ribonucleic acid and so on. Examples of recombinant proteins are erythropoietin, clotting factors, albumin, antibodies, enzymes and the like.

The foreign nucleic acid can contain regulatory elements that enable autonomous replication of the foreign nucleic acid, expression thereof or both. Such regulatory elements are known in the art and include, for example, origin of replication sequences, promoters, enhancers, splice acceptor sites, splice donor sites and polyadenylation sites. Other functional sequences can be included for a particular foreign nucleic acid. For example, a nucleic acid for encapsidation into a virus particle can contain an encapsidation sequence, such as the ψ sequence. Particular foreign nucleic acids can include, for example, inverted terminal repeats (ITR), or functional derivatives thereof, for adeno-associated virus (AAV) uses, or long terminal repeats (LTR), or functional derivatives thereof, for retrovirus uses.

"Functional derivatives" is meant to include modifications from a wild-type gene product found in a natural population that alter some of the functions of the wild-type molecule without substantially removing any desired function or functions of the product of interest. Thus, for example, the LTR's of a retrovirus for making a vector therefrom can be modified to reduce the likelihood of vector producing replication competent retrovirus (RCR) yet retaining, for example, enhancer, promoter and termination functions.

The foreign nucleic acid also can include other sequences to enhance the versatility of the foreign nucleic acid and to aid the growth thereof and identification thereof. Thus, the foreign nucleic acid can include a multiple cloning site, genes that confer a particular phenotype on the host cell, such as resistance to an antibiotic, or genes that produce a reporter molecule.

The methodologies associated with the making and using of recombinant nucleic acids are known and taught in available treatises. The artisan can resort to any of such references or make use of own known information to obtain transformed cells that can be used in the practice of the instant invention.

The particular host cells, and tissues or organs containing such host cells, are grown and maintained using known materials and methods, such as culture plates, roller bottles, reactors, fermentors, hollow fiber reactors and the like, using appropriate culture media, such as F-10, RPMI 1640 and so on, and including known additives, such as antibiotics, glutamine, indicator dyes, buffer and a serum.

In the case of a recombinant product of interest, following growth of the transformed host cells, and, if necessary, any step to yield amplification of the foreign nucleic acid introduced therein, and in the case of naturally occurring product, following growth of naturally occurring host cells of interest, the host cells are harvested by known techniques, such as centrifugation. The host cells, whether transformed or naturally occurring, may be treated to release any intracellular elements including the product of interest. Such treatment methods are known in the art and include mechanical rupture of the cells, repeated freeze-thaw treatments, enzymatic treatment, detergent treatment and so on.

Spent culture medium also may be collected if the desired product is released by the cells. For example, the desired element may be a recombinant virus particle, such as adenovirus, AAV, a retrovirus or a lentivirus, such as an HIV particle. Other desired products include recombinant gene products, such as recombinant proteins, such as hormones, clotting factors and so on. Additional desired products of interest include monoclonal antibodies, other naturally occurring molecules, such as, blood products, for example, clotting factors, cytokines, enzymes and so on.

The spent culture medium, the host cell lysate or a pool of both then is treated using known methods to obtain the desired level of purification. Such methods include centrifugation, electrophoresis, chromatography and other partitioning methods. The artisan configures the purification scheme including the number and kinds of treatments depending on, for example, the nature of the product, the conditions and the level of purity desired.

A variety of means and methods are available to determine the amount of desired product and the purity thereof during and following the isolation steps. An assay specific for the product of interest may be preferred, such as an immunoassay, a hybridization assay or other functional assay.

To determine purity, the amount or ratio of specific product as compared to a particular or a class of contaminant can be determined. For example, if the desired product is a protein, the total protein content of a sample can be determined by commercially available dye kits or by monitoring absorbance at 280 nm incident light and using a known formula to convert absorbance to concentration. Then the amount of the particular protein is determined, and the ratio to the total protein present in the sample is obtained.

Under certain circumstances, the level of a particular contaminant is monitored. For example, in virus preparations, an undesirable contaminant is replication competent retrovirus (RCR). Therefore, an assay for detecting RCR is used to monitor RCR contamination levels in a virus sample. In an antibody preparation, the amount of antibody cross-reactive with an irrelevant antigen can be tested by immunoassay using the irrelevant antigen.

A contaminant of interest is host cell nucleic acid, and particularly host cell genomic DNA. Thus, a human cell contaminant is human genomic nucleic acid. It is desirable to have an assay that can detect human DNA and thus provide an inference into the amount of human cell-generated contamination in a sample. Preferably, a means for detecting human DNA is provided that is both specific for human DNA and sensitive so that very low amounts of human DNA in a sample can be detected.

Products of recombinant DNA or genetic engineering, and naturally occurring biological products can be used in preparing a drug. Generally the biological is obtained from cells of the same species of the individuals to be treated. Thus, in the case of human, it often is desirable that the product be made or obtained from a human source, such as human cells or human tissue. Some viruses for gene delivery are produced in human packaging cells, such as human embryonic kidney cells, such as 293 cells or derivatives thereof. In such viral preparations, contamination by 293 cells or 293 cell remnants, such as DNA, is undesirable. Therefore, an assay to determine levels of 293 cells, or components thereof, in a virus preparation is used to monitor the contamination level with human host cells, or components thereof.

To meet current regulatory requirements as well as to monitor the consistency of the final human biological product, it often is necessary to monitor and to quantify residual human DNA in a preparation. Current federal guidelines relating to human biological drugs, such as a monoclonal antibody, suggest less than 100 pg of residual human host cell DNA/dose. It is desirable to have an assay that can provide such monitoring ability.

A suitable DNA detecting means providing specificity and sensitivity would be use of one or more nucleic acid probes and/or primers. Desired probe or probes would be ones that detect a particular target of the host cell genomic DNA. That can be any selected genomic sequence.

A preferred target would be the various members of a multiple copy gene family. As used herein, the individual copies that comprise a gene family of interest are identified as members, copies or elements. All of those terms and others as known in the art are considered equivalent. Preferably, the elements of the gene family of interest are distributed at multiple loci throughout the host cell genome.

Preferably the multiple loci are unlinked and found on multiple chromosomes. A suitable gene family is one that has members present on at least one-half of the chromosomes of the host cell. Preferably members of. the gene family are found on more than a half of the host cell chromosomes.

A gene family suitable for use in the instant invention can be identified by having multiple copies. Copy number can be ascertained using known techniques, such as monitoring hybridization kinetics, Southern blotting, in situ hybridization and the like. The gene family is one that has members dispersed on multiple chromosomes. That can be ascertained using known techniques, such as in situ hybridization, Southern blotting to nucleic acids of a panel of somatic cell hybrids and so on.

A suitable gene family is one that is amenable to detection by the assay of choice. For example, when doing a Southern blot, it is known what fragment sizes are maximally resolved during electrophersis and what fragment sizes bind well to the solid matrix. The fragment size can be optimized by use of endonucleases that yield fragments of desired size. In the case of PCR amplification, fragment (amplicon) size can be adjusted by choice of primers. The amplicon size is one that is amenable to amplification and detection by the selected detection means.

Thus, in the case of human, it is preferred that a member of the gene family of interest is found on at least about a half of the haploid set of human autosomes (assuming the sequence is found on both homologous pairs of each autosome), that is, on at least about 11 chromosomes of the haploid set of human autosomes. It is preferred that members of the gene family of interest are found on a majority of the human chromosomes that is on at least 12 chromosomes of the haploid set of human autosomes. It is beneficial if the gene family is distributed on a greater number of chromosomes and thus it is preferred if a sequence is found on at least 13, at least 14, at least 15, at least 16, at least 17, at least 18, at least 19, at least 20, at least 21, or on all 22 autosomes.

If the elements of the gene family are present randomly in the genome and not necessarily at the same locus on homologous chromosomes, then it is preferred that the elements of the gene family be found on at least about 22 autosomes of the diploid set that a member of the multiple gene family be found on the majority of the autosomes, that is, on at least 23 autosomes, at least 24 autosomes, at least 25 autosomes, at least 26 autosomes, at least 27 autosomes, at least 28 autosomes, at least 29 autosomes, at least 30 autosomes, at least 31, autosomes, at least 32 autosomes, at least 33 autosomes, at least 34 autosomes, at least 35 autosomes, at least 36 autosomes, at least 37 autosomes, at least 38 autosomes, at least 39 autosomes, at least 40 autosomes, at least 41 autosomes, at least 42 autosomes, at least 43 autosomes or on 44 autosomes. A gene family with individual elements distributed throughout the genome offers the advantage of monitoring presence of many, if not all of the chromosomes.

In addition to presence on theautosomes, a member of the gene family of interest also may be found on one or both of the sex chromosomes.

It also is desirable if the various members of the gene family of interest, or portions thereof, are conserved. Conservation of sequence enables detection of multiple gene family members simultaneously with a low or minimal number of probes or primers. Conservation of sequence ensures reproducibility of fragment size. Tandemly arranged copies can be beneficial because the individual copies generally are very similar if not identical in sequence and are in the same orientation. Interspersion of inverted repeats or non-repeat sequences often yields fragments of variable size and hence indistinct hybridization patterns, thereby reducing the value of such an assay for diagnostic purposes.

Those features improve on the use of a single copy gene to detect host cell genomic DNA. Detecting dispersed elements of a gene family is a robust means to monitor the presence of a large portion, if not all, of the genome. Using a widely dispersed, conserved gene family as a target would ensure that even in aneuploid cells, detection of the remainder of the chromosomes, or parts thereof, is enabled.

The characteristics of a dispersed, conserved gene family make such a gene family an ideal target for detection. Therefore, the presence of the individual, dispersed elements of a gene family can be detected by standard hybridization assays, such as Southern blots and dot blots. The hybridization assays and other in assays for detecting nucleic acids are known in the art. The artisan can obtain a suitable nucleic acid probe that hybridizes to a plurality or all of the elements of the gene family of interest. The probe can be labeled suitably as known in the art and detected by the appropriate means. The materials and methods, such as filters, stringency and so on, for conducting the hybridization assay are known in the art.

In the case of a Southern blot, an aliquot of the sample is treated with one or more suitable restriction endonucleases to fragment any genomic DNA present. In the case where the repeated elements are tandemly arranged, a single endonuclease can be used. Also, if the repeated elements contain two sites of an endonuclease that flank the complement to the probe, a single endonuclease can be used. In other circumstances, two or more endonucleases can be used to ensure that a diagnostic number of fragments containing a repeat sequence are revealed.

The endonucleases used are ones that cleave the genomic DNA to yield a resolvable fragment containing sequences recognizable by a probe of the gene family of interest. The DNA is displayed by electrophoresis and then the fragments are manipulated to enable hybridization with the probe, for example, the nucleic acids are rendered single-stranded.

The probe is one that is manipulated to contain a reporter molecule, such as a radionuclide, an antigenic determinant, an enzyme or a fluorogenic molecule. Alternatively, the probe is not labeled in any particular way but is detectable, for example, by a particular antibody specific for the probe molecule or one that is specific for double stranded nucleic acid. The probe is allowed to hybridize to the separated, denatured genomic DNA. The complexes are washed at the appropriate stringency to ensure specificity and the duplexes visualized by the appropriate means.

In the case of dot blots, an aliquot of the sample is applied to a matrix, such as a membrane filter. The DNA is rendered single-stranded and then exposed to probe as described hereinabove. The probe may or may not be labeled at the discretion of the artisan. The procedure essentially is as described for Southern blotting.

Because the genomic target of interest comprises a multiple gene family, amplification may not be essential. However, the artisan is free to employ an amplification means as known in the art. The sensitivity of an assay of interest may be enhanced by an amplification means.

The elements of a gene family that are relatively well conserved are amenable also to amplification methods. Both transcription-based and translation-based amplification methods can be used. Therefore, polymerase chain reaction (PCR), ligase chain reaction (LCR) and so on amplification of human genomic DNA can be practiced. Transcription-based amplification methods, such as transcription-based amplification system (TAS), NASBA and 3SR also can be used when the targeted repeat sequence is expressed. The amplification methods are known in the art and the artisan is free to employ an amplification method of choice so long as specificity and sensitivity are not compromised.

The detection of elements of a gene family of interest by the methods taught hereinabove can be by any known means, such as use of radionuclide reporter molecules, fluorogenic or fluorescent reporter molecules and so on, as known in the art. The particular reporter molecule used is combined with appropriate detection means. Thus, in the case of a fluorescent reporter molecule, signal can be monitored by laser scanning and be detected by a charge coupled device (CCD) camera Nonspecific background fluorescence can be monitored throughout amplification by the presence of a passive fluorescent dye in the reaction buffer.

When amplification is practiced, a genomic or DNA amplification method may be preferred. In the case of PCR, the artisan develops the suitable primers that frame the amplicon. Preferably the primers are ones that frame a sequence conserved in many, if not all, of the elements of the gene family of interest. Also, the primers are selected to yield an amplicon easily revealed and resolvable. The making of the primers, selection of the primers to produce a suitable amplicon, the cycling conditions and methods for detecting the amplicons are as known in the art.

The human endogenous retrovirus-like (HERV) gene family satisfies the above criteria as a means for detecting the presence of human genomic DNA. In the case of the HERV-H family, approximately 2,000 copies of HERV-H elements, dispersed throughout the genome, are present in a diploid human cell (Wilkinson et al., J. Virol. 64:2157, 1990; Mager & Henthorn, Proc. Natl. Acad. Sci. 81:7510–7514, 1984; Fenchter et al., Genomics 13:1237–1246, 1992; Fraiser et al., Genomics 2:280–287, 1988).

When PCR amplification is used, practicing known methods and employing suitable primers configured based on the HERV-H sequence to amplify a conserved portion of the HERV-H elements, 1 pg of human DNA can be detected reproducibly. The assay can detect as little as 10 fg of human DNA.

All references cited herein are incorporated by reference herein in entirety.

The examples provided hereinabove are for exemplification purposes only and are not to be construed as limiting of the invention. It will be clear to the artisan that various modifications and changes can be made to the teachings herein without departing from the spirit and scope of the invention.

We claim:

1. A method for determining an amount of human host cell genomic DNA in a biological product isolated or purified from the human host cell or spent culture medium, said method comprising:
   (a) hybridizing at least one nucleic acid probe and/or at least one primer to a human endogenous retrovirus-like H (HERV-H) gene family genomic DNA in said biological product, wherein said probes and/or primers specifically hybridize to said HERV-H gene family genomic DNA;
   (b) detecting said probe or said primer bound to said HERV-H gene family genomic DNA;
   (c) determining an amount of said HERV-H gene family genomic DNA in said biological product; and
   (d) determining an amount of host cell genomic DNA in said biological product based on the amount of said HERV-H gene family genomic DNA in said biological product.

2. The method of claim 1, wherein said biological product comprises adenovirus.

3. The method of claim 1, wherein said biological product comprises adeno-associated virus.

4. The method of claim 1, wherein said biological product comprises retrovirus.

5. The method of claim 4, wherein said retrovirus is a lentivirus.

6. The method of claim 1, further comprising lysing host cells in said biological product prior to detecting the amount of said HERV-H gene family genomic DNA in said biological product.

7. The method of claim 1, wherein said human host cells are human embryonic kidney cells.

8. The method of claim 7, wherein said human embryonic kidney cells are derived from 293 cells.

9. The method of claim 7, wherein said embryonic kidney cells are 293 cells.

10. The method of claim 1, wherein said biological product comprises a protein.

11. The method of claim 10, wherein said protein is an antibody.

12. The method of claim 11, wherein said antibody is a monoclonal antibody.

13. The method of claim 10, wherein said protein is a recombinant protein.

14. The method of claim 1, further comprising an amplification reaction prior to determining the amount of said HERV gene family genomic DNA in said biological product.

15. The method of claim 14, wherein said amplification reaction is a polymerase chain reaction (PCR).

16. The method of claim 15, wherein said PCR comprises a fluorescent label.

* * * * *

UNITED STATES PATENT AND TRADEMARK OFFICE
CERTIFICATE OF CORRECTION

PATENT NO. : 6,864,053 B1
DATED : March 8, 2005
INVENTOR(S) : John M. Irving et al.

It is certified that error appears in the above-identified patent and that said Letters Patent is hereby corrected as shown below:

Title page,
Item [73], Assignee, "Cell Genesys Foster City, CA (US)" change to
-- Cell Genesys, Inc. South San Fransisco, CA (US) --.

Column 3,
Line 35, change "glutarnine" to -- glutamine --.

Column 5,
Line 4, delete ".";
Line 50, "autosomes, at least 31, autosomes," change to -- autosomes, at least 31 autosomes, --
Line 59, change "theautosomes" to -- the autosomes --.

Signed and Sealed this

Twenty-sixth Day of July, 2005

JON W. DUDAS
*Director of the United States Patent and Trademark Office*